(12) United States Patent
Budinger et al.

(10) Patent No.: US 7,896,530 B2
(45) Date of Patent: Mar. 1, 2011

(54) AIRCRAFT HAVING AN ILLUMINATION DEVICE

(75) Inventors: Tilo Budinger, Hamburg (DE); Carsten Vogel, Hamburg (DE)

(73) Assignee: Airbus Deutschland GmbH (DE)

( * ) Notice: Subject to any disclaimer, the term of this patent is extended or adjusted under 35 U.S.C. 154(b) by 355 days.

(21) Appl. No.: 12/075,136

(22) Filed: Mar. 7, 2008

(65) Prior Publication Data
US 2008/0219013 A1 Sep. 11, 2008

Related U.S. Application Data

(60) Provisional application No. 60/905,372, filed on Mar. 7, 2007.

(30) Foreign Application Priority Data

Mar. 7, 2007 (DE) .......................... 10 2007 011 155

(51) Int. Cl.
*F21V 21/00* (2006.01)
(52) U.S. Cl. ....................................................... 362/471
(58) Field of Classification Search .................. 362/471, 362/470, 472
See application file for complete search history.

(56) References Cited

U.S. PATENT DOCUMENTS

| | | | | |
|---|---|---|---|---|
| 6,203,180 B1 * | 3/2001 | Fleischmann | ................. | 362/471 |
| 6,554,439 B1 * | 4/2003 | Teicher et al. | .................... | 362/2 |
| 2005/0237766 A1 | 10/2005 | Klettke | | |

FOREIGN PATENT DOCUMENTS

| | | |
|---|---|---|
| DE | 3123371 | 12/1982 |
| DE | 10232797 | 1/2004 |
| DE | 102004020122 | 12/2005 |
| EP | 1561640 | 8/2005 |
| GB | 2101549 | 1/1983 |

OTHER PUBLICATIONS

Berson, D.M., Dunn, F.A., Motoharu Takao: "Phototransreduction by retinal ganglion cells that set the circadian clock", Science, Feb. 8, 2002.
Wout van Bommel, Gerrit van den Beld, Philips Lighting, The Netherlands: "Lighting for work: Visual and biological effects", Apr. 2003.
Schierz, C.: "Do we live in the "biological darkness"?", Licht 2002/ Light 2002; from Sep. 22 to Sep. 25, 2002 in Maastricht; Volume of the convention, p. 318-389.
Wiemers, S.: "Vigilanzleuchte im Kraftfahrzeuges" (2006).
Krämer, André: "Blauer Himmel in der Nacht; Sicherheit / Neue Leuchte gegen Sekundenschlaf" Autohaus S. 2; 14-15/2006.

(Continued)

*Primary Examiner* — John A Ward
(74) *Attorney, Agent, or Firm* — Lerner, David, Littenberg, Krumholz & Mentlik, LLP

(57) ABSTRACT

An illumination device and an aircraft having an illumination device which by a corresponding selection of the wavelength and of the irradiation angle prevents a person situated in the aircraft from becoming tired. The illumination device is arranged in an aircraft such that light given off by the illumination device can be irradiated onto the retinohypothalamic tract of a person who is present in the aircraft in a predetermined position, and the illumination device is designed to give off light at a predetermined wavelength, which light achieves the desired effect.

15 Claims, 4 Drawing Sheets

OTHER PUBLICATIONS

Gall, Dietrich: "Importand aspects to be considered when you have to choose a beneficial spectrum of lamps" Part 1: General aspects to be considered when you have to choose a lamp (2003).

Gall, Dietrich: "Gall, Dietrich: Importand aspects to be considered when you have to choose a beneficial spectrum of lamps" Part 2: Circulation light values and their metrological determination (2003).

Mark S. Rea, Ph.D.: "Light-Much More Than Vision, Lighting", Research Center, Rensselaer Polytechnic Institute, Troy, NY, USA 12180 (2003).

* cited by examiner

AIRCRAFT HAVING AN ILLUMINATION DEVICE

CROSS-REFERENCE TO RELATED APPLICATIONS

This application claims the benefit of the filing date of U.S. Provisional Patent Application No. 60/905,372 filed Mar. 7, 2007, the disclosure of which is hereby incorporated herein by reference.

BACKGROUND OF THE INVENTION

The present invention relates to an aircraft having an illumination device, and in particular to an aircraft having an illumination device which by a corresponding selection of the wavelength and of the irradiation angle prevents a person situated in the aircraft from becoming tired or sleepy.

There exists a biological light effect on humans that acts as a result of the action of light of a particular wavelength on certain regions in the eye. These regions are outside the eye's region that is responsible for visual perception. It has been recognised that the action of light falling onto the retinohypothalamic tract affects, for example, control of the hormone melatonin, which hormone is responsible for controlling tiredness and wake states, and further affects regulation of the circadian rhythm, which reflects the change between the wake state and the state of tiredness or sleepiness. The retinohypothalamic tract is an arrangement of photosensitive cells on the retina, which cells occur in an aggregated manner on the lower part of the retina. These cells comprise the light-sensitive pigment melanopsin that converts light to electrical signals. The so-called suprachiasmatic nucleus (SCN) is driven by these signals and influences the pineal gland, which in turn regulates hormone release. This hormone control then provides the corresponding predetermined values for setting the inner biological clock of humans. For this reason an increase in the melatonin level, for example at night, results in considerable tiredness or sleepiness, while a reduction in the level of sleep hormone sets the organism to "waking up". This non-optical system reacts best to essentially monochromatic light with a wavelength of 464 nanometres, which essentially corresponds to the blue colour of the sky. If a special non-optical receptor in the eye, which receptor is preferably found in the lower half of the retina, is irradiated with short-wave light of approximately 464 nanometres, then melatonin production stops so that melatonin suppression occurs. In this process, even small quantities of light of a wavelength of 464 nanometres are sufficient to influence melatonin production.

SUMMARY OF THE INVENTION

There may be a need to provide an aircraft with an illumination device that acts on the wake state or on the state of tiredness or sleepiness of persons in the aircraft such that this wake state or the state of tiredness or sleepiness can be influenced.

According to an exemplary embodiment of the invention, an aircraft comprises an illumination device, wherein the illumination device is arranged in a region of the aircraft such that light given off by the illumination device is irradiated onto the retinohypothalamic tract of a person who is present in an aircraft in a predetermined position, and the illumination device is designed to give off light at a wavelength of between 440 nanometres and 480 nanometres.

Such an illumination device affects persons present in an aircraft and their circadian rhythm so that said illumination device by corresponding control can be used to adjust this circadian rhythm of passengers and flight crew in order to influence their inner biological clocks. This is, for example, advantageous in cases where persons fly through various time zones. Shifting the circadian rhythm can, for example, be achieved by activating the day cycle by exposure to light of a wavelength of between 440 nanometres and 480 nanometres. Furthermore, in the region of the cockpit, too, exposure of the pilots or of cabin crew to light of a wavelength of between 440 nanometres and 480 nanometres outside the fields of view, the day cycle of the people can be initiated or maintained, as a result of which, generally speaking, vigilance e.g. the wake state, increases. In this context the expression "intended position" refers, for example, to a standard seating position of a passenger or of a pilot in a corresponding seat, so that the illumination device is then placed in a suitable position, by a person skilled in the art, such that in a normal intended head position the light given off by the illumination device shines on the retinohypothalamic tract in the eye.

According to an exemplary embodiment of the invention, the illumination device is designed such that the light given off is a light with a wavelength of essentially 464 nanometres plus/minus 10 nanometres. According to a further exemplary embodiment, the wavelength is essentially 464 nanometres plus/minus 5 nanometres.

It has been shown that exposure to light at a wavelength of 464 nanometres has an influence on the release of the hormone melatonin so that with the use of this wavelength an influence on the day cycle or night cycle can be achieved.

According to an exemplary embodiment of the invention, the illumination device in a general illumination device is provided such that the illumination device can be controlled separately.

In this way targeted activation of the illumination device can take place, wherein the light given off by the illumination device can also be superimposed by light given off by a general illumination device, without this influencing the effect on vigilance. However, as a result of such integration in general illumination, passengers or the crew do not necessarily perceive the illumination as blue illumination, so that any influencing is also not necessarily perceived any longer by persons present in the aircraft.

According to an exemplary embodiment of the invention, the aircraft comprises a control device for the illumination device, wherein the control device is designed to control the illumination device in relation to intensity, point in time and period of time.

In this way over time a defined illumination pattern can be created whose intensity varies over time so that the circadian rhythm of the passengers or of the crew can be modified.

According to an exemplary embodiment of the invention, the control device is designed to control the illumination device depending on a predeterminable circadian rhythm.

For example, if one or several time zones are traversed, the illumination device can be controlled such that the wake cycle or the cycle of tiredness or sleepiness is shifted such that passengers and also the air crew cope more easily with time differences, and such that the effects of jetlag are reduced. This can, for example, take place by adapting the circadian rhythm to the time zone of the destination airport. Furthermore, in particular in the case of pilots, the wake state can be maintained even at times in which according to the natural circadian rhythm they would be in a phase of tiredness or sleepiness, so that by avoiding tiredness in the aircrew, generally speaking, flight safety can be enhanced.

According to an exemplary embodiment of the invention, the illumination device can be arranged accordingly in the cockpit and/or in a passenger cabin of an aircraft.

According to an exemplary embodiment of the invention, the illumination device is situated outside the field of view of the person who is present in the predetermined position.

In this way the illumination is no longer visually perceived by the person concerned, so that in particular also pilots in the cockpit, even when the cockpit is darkened, are not influenced or irritated by such illumination.

According to an exemplary embodiment of the invention, the illumination device is integrated in a ceiling lining or a wall lining.

In this way conscious perception of the illumination device can be further prevented so that its effect as a result of illumination is no longer consciously perceived by the person concerned.

According to an exemplary embodiment of the invention, the illumination device comprises at least one LED or OLED as an illumination means.

A light-emitting diode (LED) or an organic light-emitting diode (OLED) on the one hand comprises an easily adjustable light spectrum that can be selected so as to be sufficiently narrow for the corresponding application case, and on the other hand comprises only very small installation dimensions and consumes only relatively little power.

According to an exemplary embodiment of the invention, the illumination device comprises a diffusion device so that any blinding effect, for example when a person unintendedly looks directly at the illumination device, can be prevented. Furthermore, the radiation region is also enlarged by a diffusion device, so that there is a higher probability of the corresponding receptors in the eye being reached by the light given off by the illumination device.

According to an exemplary embodiment of the invention, the aircraft comprises several illumination devices that can be controlled independently of each other.

In this way it is possible, for example, in a targeted manner to bring about a state of tiredness or sleepiness in the passengers, and subsequently, in a timely manner so as to match the time zone of the destination airport, to initiate a wake state, while in the case of the aircrew the priority is rather on maintaining the wake state during the entire flight so as to ensure the safety of the flight. It is thus advantageous, for example, to control an illumination device in a passenger cabin with timing that differs from the timing of such an illumination device in a cockpit. Furthermore, it can be provided for the passengers themselves to select the time-related illumination profile individually, for example if they intend to board a connecting flight to destinations that in turn are located in different time zones.

It should be understood that the individual characteristics described above can also be combined to the extent that this appears sensible to a person skilled in the art.

Below, detailed exemplary embodiments of the invention are now described and clarified with reference to the drawings.

BRIEF DESCRIPTION OF THE DRAWINGS

Exemplary embodiments of the present invention are described below with reference to the following drawings.

DETAILED DESCRIPTION

Figure 1:
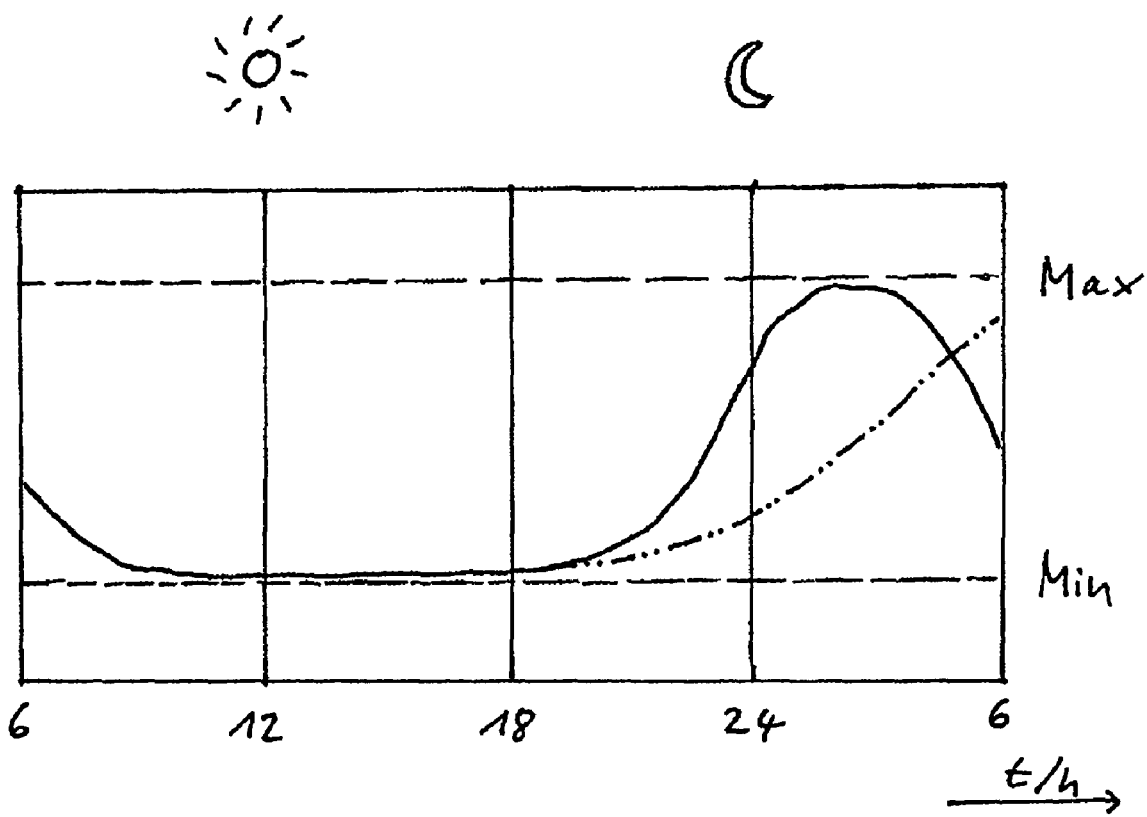
FIG. 1 shows a circadian rhythm of a person.

FIG. 1 shows a circadian rhythm, also referred to as an internal clock, of a person. The diagram shows a concentration, between the minimum and the maximum, of the hormone melatonin over a period of a day between 6 am on one day and 6 am on the following day. As the night ends after 6 am the melatonin content drops so that the human body wakes up. During the course of the day the melatonin level stays at a low level, which among other things is supported in that at least on days without full cloud cover irradiation of light with the colour of the blue of the sky keeps the melatonin level low. After the natural course of the day, at dusk, the low melatonin level cannot be kept at a low level because there is no corresponding coloured light irradiation of the eye, for example by the blue sky. The melatonin level therefore continuously rises, for example after 6 pm, until it has reached its maximum in the middle of the night, which happens essentially in accordance with the normal sleep habits of a person. However, if the person experiences a backward time difference as a result of traversing time zones, it is possible, for example, by artificial irradiation of light of a wavelength of, for example, 464 nanometres, to further delay the release of the hormone melatonin, as shown by the dot-dash line in the diagram. The maximum melatonin level is thus achieved only at a later time so that the internal clock or the circadian rhythm of the person can be set to the time zone, for example, of the destination airport.

With reference to a practical example this means, for example, that during flights with an east or a west component the crew and the passengers traverse different world time zones. The destination airport is thus in a time zone that differs from the time zone of the departure airport, wherein it is possible for the time zone to be different by a maximum of plus/minus 12 hours. However, due to the lack of daylight irradiation/irradiation of the light from the sky, the circadian rhythm or the internal clock of the human organism cannot adjust itself independently to a new time zone during the flight. In general language use this effect is commonly referred to as "jetlag". Tiredness or sleepiness in the evening in the circadian rhythm is associated with the release of melatonin, which is generally known as the "sleep hormone". In other words the increase of the melatonin level during the night results in greater tiredness or sleepiness, while a reduction in the sleep hormone level sets the organism to "waking up", as is shown in FIG. 1 in the region between 6 am and noon. By way of suppressing melatonin production in the human organism during the night phase, vigilance, i.e. the state of being awake, of both passengers and flight crew can be increased during the entire flight. In this way it is possible to counteract continuous tiredness or sleepiness of the aircrew. Passengers can in a targeted manner be shifted to the "day phase", as a result of which the jetlag effect can be significantly reduced.

Figure 2:
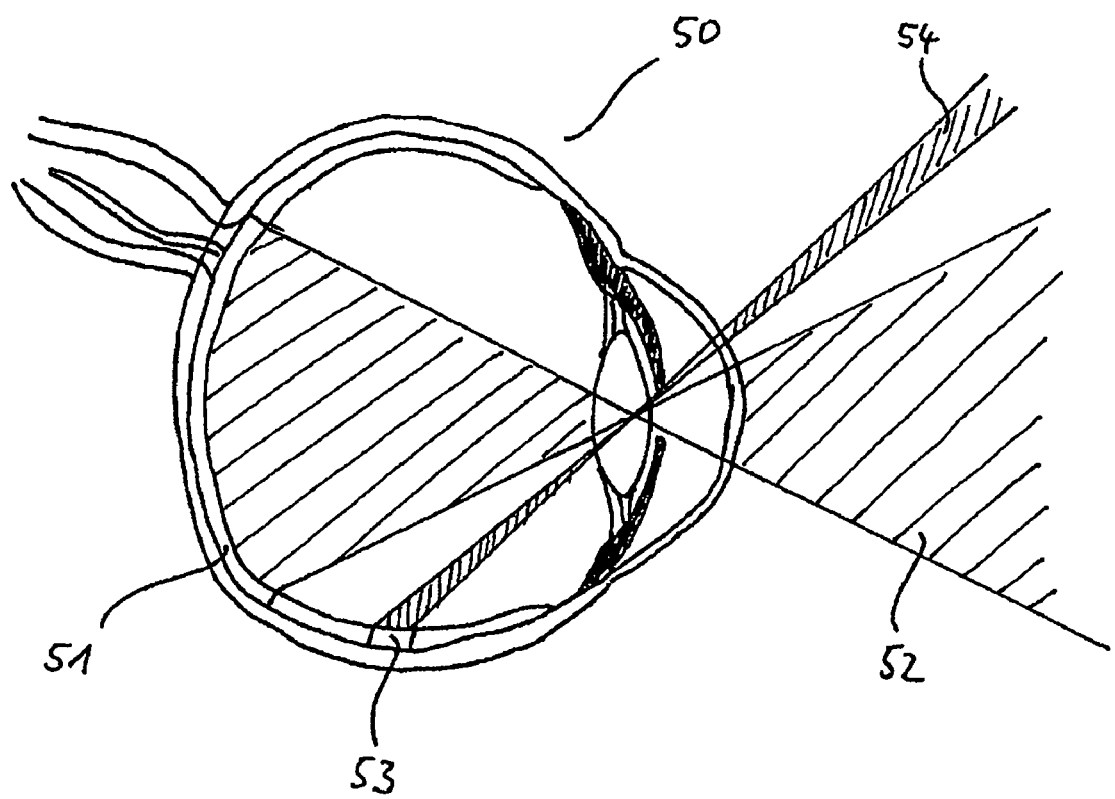
FIG. 2 shows a section view of a human eye.

FIG. 2 shows a section view of the human eye 50. Parallel to the optical system 51, for example in the form of the light-sensitive retina, there is a non-optical system that also comprises the retinohypothalamic tract 53. This system transmits purely biological occurrences, among other things the control of melatonin production at night, and thus the regulation of the circadian rhythm and the influence on the degree of being awake. Light-sensitive cells, so-called ganglion cells, which in the human eye are predominantly arranged at the lower part of the retina, form the initial point of the cause-effect chain. These cells comprise the light-sensitive pigment melanopsin which converts light to electrical signals. These signals control the suprachiasmatic nucleus (SCN) which in turn influences the pineal gland, which is responsible for melatonin release.

This non-optical system 53 best reacts to irradiation of the cells in the eye with monochromatic light at a wavelength of approximately 464 nanometres, which essentially corresponds to the blue of the sky. The angle of incidence or the region of irradiation 54 is above the field of view 52. At this stage it should be mentioned that in FIG. 2 refraction due to different refractive indices has not been taken into account in the graphic depiction of the human eye.

The fact that these light-sensitive ganglion cells are situated in the lower part of the eye makes it necessary for light at the effective wavelength to enter the eye obliquely from above, as shown in FIG. 2 by reference character 54. The reason for this can be found in the natural control of the described cause-effect chain by the light from the sky.

As far as the general illumination of the aircraft passenger cabin is concerned this means that in addition to the illumination means in the general illumination, for example in the form of RGB (red-green-blue), which illumination means are designed for optimum colour generation, a corresponding light source with a wavelength of, for example, approximately 464 nanometres has to be provided. In this arrangement the wavelength can have a tolerance of plus/minus 10 nanometres, or of plus/minus 5 nanometres.

Illumination from both the general illumination device and from the illumination device with a wavelength of approximately 464 nanometres can take place by light-emitting diodes (LEDs) or by organic light-emitting diodes (OLEDs), because they comprise not only a colour light spectrum that can be set very well, but they are also associated with small installation dimensions and modest power consumption.

These LEDs or OLEDs, which are effective in modifying the circadian rhythm, are, for example, controlled separately, i.e. their intensity can be controlled at any time by the light control system for the general cabin illumination.

Figure 3:
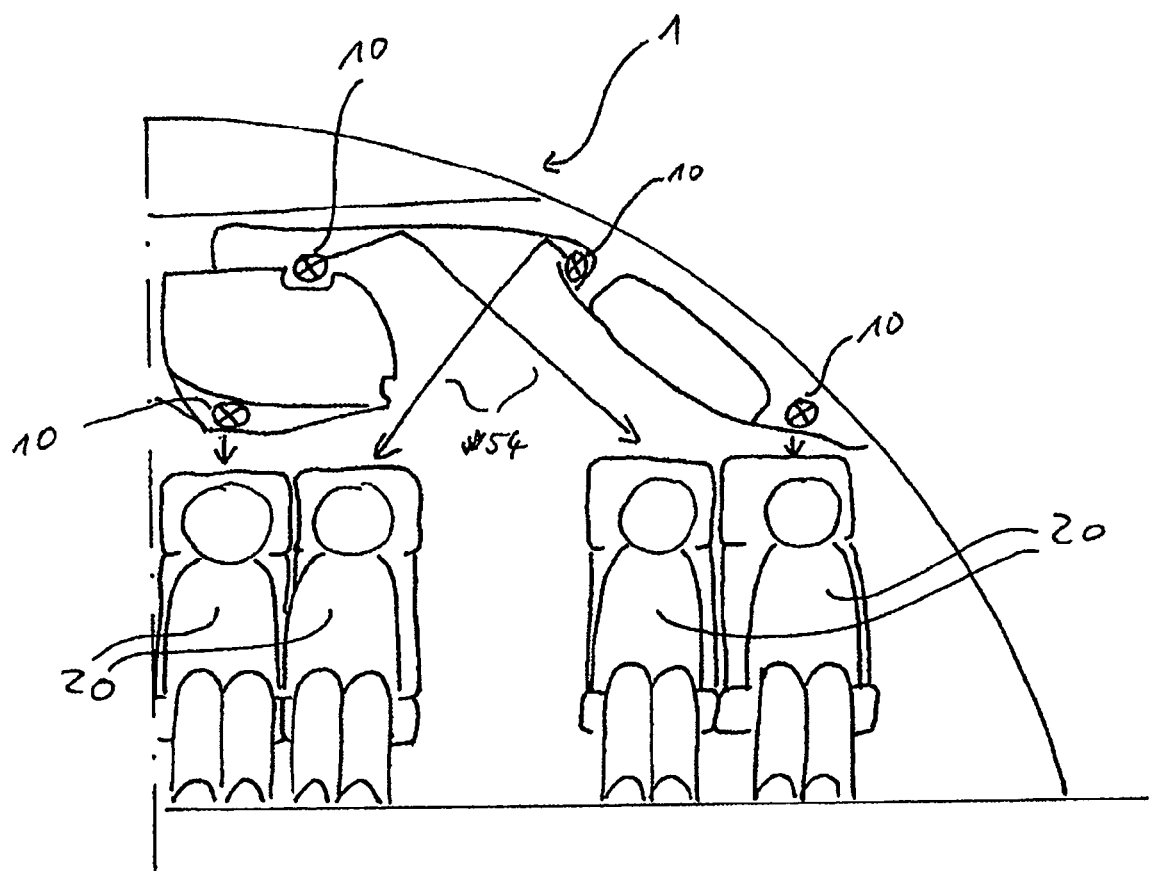
FIG. 3 shows a cross section of a cabin segment with possible installation positions of an illumination device in an aircraft.

FIG. 3 shows an exemplary arrangement of various illumination devices 10, each arranged such that it is above the field of view of a person 20 present in the intended position. In this arrangement the light is radiated to a region of incidence 54 that has already been described with reference to FIG. 2. It should be mentioned that the illumination devices can irradiate both directly and by way of reflection, for example from the cabin ceiling, wherein the cabin ceiling then has to be designed such that no absorption occurs in the relevant wavelength range, in the present case of approximately 464 nanometres.

It is understood that the scope of protection of the present invention also covers arrangements in which the illumination device gives off a light of some other wavelength, and in which the relevant wavelength of, for example, 464 nanometres only occurs after a wavelength conversion, similar to the case of fluorescent tubes.

Figure 4:
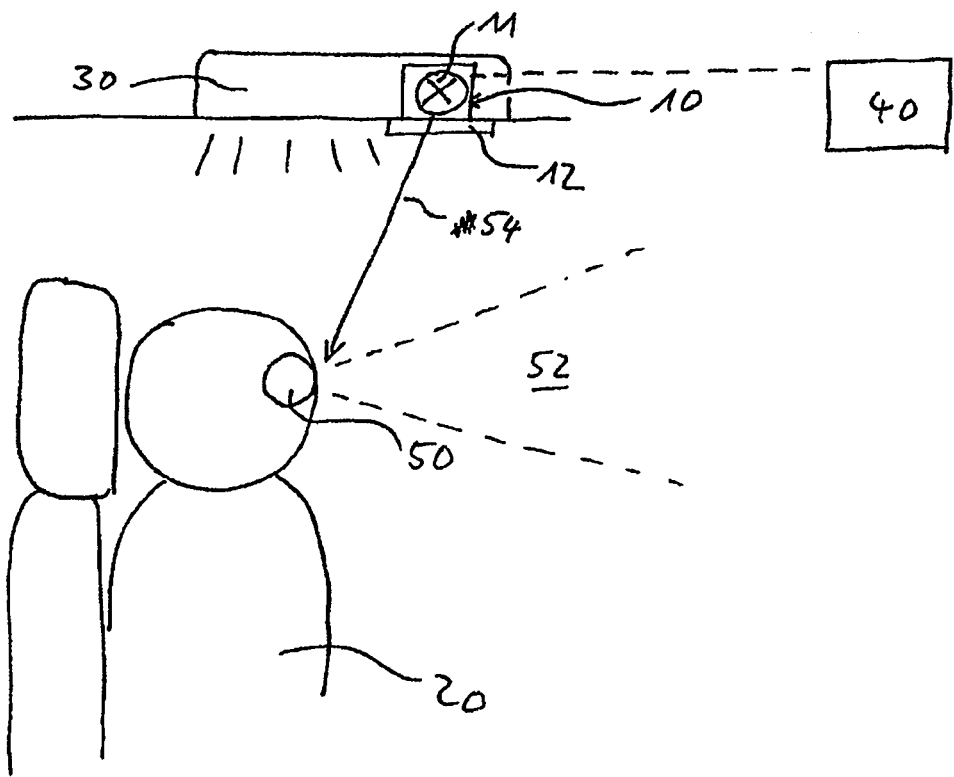
FIG. 4 shows a lateral section view of a possible position arrangement of an illumination device according to an exemplary embodiment of the invention.

Since the light sources for general illumination in the standard illumination system, in which the illumination device is implemented, are basically arranged above the horizontal plane of view of the passengers 20, entry of the effective radiation into the eyes of the passengers 20 at an inclined angle from above is ensured, as shown in FIGS. 3 and 4. It is understood that the same also applies to corresponding positions for the cabin crew or the cockpit crew.

Exposing the cabin crew to radiation that is effective in modifying the circadian rhythm can, for example, take place by way of spotlights, reading lamps, attendant work lights etc., because these are basically arranged above the field of vision. The light-emitting diodes that are effective in modifying the circadian rhythm can additionally be integrated in these lamps. In the region of the cockpit these light-emitting diodes or organic light-emitting diodes that are effective in modifying the circadian rhythm can be provided in separate lamps because in a cockpit it is advantageous if only light-emitting diodes or organic light-emitting diodes with a wavelength of 464 nanometres plus/minus, for example, 5 nanometres are integrated in a lamp. This lamp is, for example, arranged above and outside the field of view of a pilot in the cockpit so that, for example, a region of incidence 54 results, as described with reference to FIG. 2, which region of incidence 54 provides for light incidence onto the corresponding receptor region 53 in the human eye 50. The light distribution of such a lamp can be diffused by a suitable diffusing disc or a diffuser so that the absence of any glare is ensured in particular in the cockpit.

FIG. 4 shows an exemplary arrangement of an illumination device 10 with an illumination means 11 in a general illumination device 30, wherein in this embodiment a diffuser 12 is provided in front of the illumination device 10. The illumination device can, for example, be controlled by a control device 40. With a further control device (not shown) the general illumination device 30 can be controlled independently of the control of the illumination device 10. The light 54 given off by the illumination device 10 is outside the visual range 52 of the human eye 50 of a passenger 20. In such a position a passenger 20 (or a pilot) does not experience any irritation as a result of the illumination device 10.

With the control device 40 it is, for example, possible to set light profiles with variable intensity depending on points in time and periods of time such that, for example, for a pilot permanent light irradiation is maintained during the entire flight time so as to suppress the release of the hormone melatonin, while, for example, for a passenger, by suitable matching, the wake state can be restored in a time region that coincides with the time zone of the destination airport. Control can also be provided individually for each passenger or group of passengers. If prior to boarding it is already known which passengers are booked on the same connecting flight to a further, other, time zone, then these passengers can be grouped, and the exposure of the light that influences the circadian rhythm can be uniformly controlled in the seating region of this group of passengers.

It is understood that by a corresponding setting of the intensities and points in time of the illumination by the illumination device, for example at a wavelength of 464 nanometres, various physiological factors can also be influenced so that, by correspondingly adapting the control regime, the overall wellbeing of passengers, in particular in the case of long-haul flights with an east-west component, can be significantly enhanced.

The light source that is effective in modifying the circadian rhythm is thus on the one hand in a position, by targeted application, to prevent tiredness or sleepiness from arising, and on the other hand to adapt the circadian rhythm, for example of passengers, to the time zone of the destination airport such that any jetlag effect can be reduced or prevented. The system is associated with an advantage in that it aims directly at the cause of tiredness or sleepiness, rather than coming into effect only when tiredness or sleepiness arises or is already in existence.

In addition, it should be pointed out that "comprising" does not exclude other elements or steps, and "a" or "an" does not exclude a plural number. Furthermore, it should be pointed out that features or steps which have been described with reference to one of the above exemplary embodiments can also be used in combination with other features or steps of other exemplary embodiments described above. Reference characters in the claims are not to be interpreted as limitations.

The invention claimed is:

1. An aircraft having an illumination device,
   wherein the illumination device is arranged in the aircraft such that light given off by the illumination device is irradiated onto the retinohypothalamic tract of a person who is present in the aircraft in a predetermined position, wherein the illumination device emits only light at a wavelength of between 440 nm and 480 nm.

2. The aircraft of claim 1, wherein the illumination device emits light with a wavelength of essentially 464 nm +/−10 nm.

3. The aircraft of claim 1, wherein the illumination device is provided in a general illumination device such that the illumination device can be controlled separately.

4. The aircraft of claim 1, comprising a control device for the illumination device to control the illumination device in relation to intensity, point in time and period of time.

5. The aircraft of claim 4, wherein the control device controls the illumination device depending on a predeterminable circadian rhythm.

6. The aircraft of claim 1, wherein the illumination device is arranged in a cockpit of the aircraft.

7. The aircraft of claim 1, wherein the illumination device is arranged in a passenger cabin of the aircraft.

8. The aircraft of claim 1, wherein the illumination device is situated outside the field of view of the person who is present in the predetermined position.

9. The aircraft of claim 1, wherein the illumination device is integrated in a ceiling lining or a wall lining.

10. The aircraft of claim 1, wherein the illumination device comprises at least one light-emitting diode or an organic light-emitting diode.

11. The aircraft of claim 1, wherein the illumination device comprises a diffusion device.

12. The aircraft of claim 1, further comprising a plurality of illumination devices that can be controlled independently of each other.

13. An aircraft having an illumination device,
    wherein the illumination device is arranged in the aircraft such that light given off by the illumination device is irradiated onto the retinohypothalamic tract of a person who is present in the aircraft in a predetermined position, and the illumination device is designed to only give off light at a wavelength of 464 nm +/−5 nm.

14. An aircraft having an illumination device,
    wherein the illumination device is arranged in the aircraft such that light given off by the illumination device is irradiated onto the retinohypothalamic tract of a person who is present in the aircraft in a predetermined normal seating position, and the illumination device is designed to only give off light at a wavelength of between 440 nm and 480 nm.

15. An aircraft having an illumination device,
    wherein the illumination device is arranged in an aircraft such that light given off by the illumination device can be irradiated onto the retinohypothalamic tract of a person who is present in the aircraft in a predetermined position,
    wherein the illumination device emits light at a wavelength of between 440 nm and 480 nm to delay the release of melatonin in the person to increase the period of time for which the person remains awake.

* * * * *